United States Patent [19]

Rosen et al.

[11] Patent Number: 5,637,571
[45] Date of Patent: Jun. 10, 1997

[54] USE OF LIGNAN DERIVATIVES FOR THE PREPARATION OF PHARMACEUTICAL COMPOSITIONS FOR THE TREATMENT OF STATES OF AMYLOIDOSIS

[75] Inventors: Borje Rosen, Vallentuna, Sweden; Kurt Leander, Peseux, Switzerland

[73] Assignees: Conpharm AB, Uppsala, Sweden; Analytecon SA, Couvet, Switzerland

[21] Appl. No.: 553,423
[22] PCT Filed: May 25, 1994
[86] PCT No.: PCT/SE94/00493
§ 371 Date: May 10, 1996
§ 102(e) Date: May 10, 1996
[87] PCT Pub. No.: WO94/27614
PCT Pub. Date: Dec. 8, 1994

[30] Foreign Application Priority Data

May 28, 1993 [SE] Sweden ................................... 9301831

[51] Int. Cl.⁶ ................................................. A61K 31/70
[52] U.S. Cl. ............................................................ 514/27
[58] Field of Search ................................................. 514/27

[56] References Cited

U.S. PATENT DOCUMENTS 4,788,216 11/1988 Leander et al. .......................... 514/468

FOREIGN PATENT DOCUMENTS 823068 11/1959 United Kingdom .

OTHER PUBLICATIONS

Truedsson et al, Clinical and Experimental Rheumatology, 11:179–182 (1993).
Dahlqvist et al, British Journal of Rheumatology, 28:418–421 (1989).

*Primary Examiner*—Theodore J. Criares
*Attorney, Agent, or Firm*—Birch, Stewart, Kolasch & Birch, LLP

[57] ABSTRACT

This invention relates to the treatment of a host afflicted with a state of secondary amyloidosis using certain acetals of podophyllotoxin-β-D-glucopyranoside.

4 Claims, No Drawings

USE OF LIGNAN DERIVATIVES FOR THE PREPARATION OF PHARMACEUTICAL COMPOSITIONS FOR THE TREATMENT OF STATES OF AMYLOIDOSIS

The present invention refers to the use of certain lignan derivatives for the preparation of pharmaceutical compositions for the treatment of certain diseases. More specifically, the invention refers to the use of certain acetals of podophyllotoxin-β-D-glucopyranoside and 4'-demethylpodophyllotoxin-β-D-glucopyranoside for the preparation of pharmaceutical compositions for the treatment or prophylaxis of states of amyloidosis. Furthermore, the invention refers to a method for treatment of a host afflicted with a state of amyloidosis.

Amyloidosis is the general name of states or diseases where amyloid is present in a host systemically or locally. The amyloid tissues are characterized by a content of amyloid, which is a collective name for a chemically heterogenous substance having certain characteristic properties. It is known that a common feature of amyloid is a specific secondary and tertiary structure wherein small proteins (molecular weight from 3000 to about 30,000 Daltons) are stacked on each other and are bonded to each other via hydrogen bonds to so-called beta-sheets, which give thin fibrils. These fibrils, which have a diameter of about 7.5 nanometers and can only be seen in an electron microscope, constitute the main material of all amyloid substance. A number of different proteins have the property of forming fibrils in this way, but only one single protein builds up the fibril in the particular deposition. The protein fibril constitutes the core of the amyloid substance and gives this substance some of its characteristic properties, such as a resistance against enzymatic and other degradation, and some staining properties which are important in practice. Other components are also present in all amyloid substance.

The amyloid fibrils are formed at the site of the incorporation. It is not yet known whether the fibrils are formed extracellularly or intracellularly. The proteins forming part of the fibrils can either be synthesized in cells at the site of the incorporation (local amyloidosis) or at some other site, such as the liver or the bone marrow, and be transported to the site of the incorporation by plasma (systemic amyloidosis).

A number of different types of amyloid are known, depending on the type of protein which forms the fibrils. However, all types of amyloid are regarded as pathological, and normally occurring amyloid fibrils have never been found. A consequence of this is that all amyloid is an expression of an abnormal formation of fibrils. It is not yet known why the amyloid fibrils are not degraded but are instead incorporated progressively. One explanation of this may lie in the strong intermolecular bonds in the fibril, and possibly also in a protective sheathing of proteoglycans. It may be noted that the amyloid hardly ever gives rise to any inflammatory reaction.

The pathogenetic importance of the amyloid substance lies to a large degree in the space which the substance occupies, with a consequent atrophy of the surrounding tissue. The amyloid, which is deposed between cells and between groups of cells and vessels, probably hinders the transport of nourishments and other substances. The cell membranes may be damaged by penetrating fibrils. Furthermore, the amyloid substance seems to affect the basal membranes, at least in the glomeruli, so that the filtering efficiency is degraded.

Amyloidosis has been observed in association with a number of diseases, such as certain mental illnesses, neurological diseases and collagenosis. Among the various types of mental illness in this connection may be mentioned Alzheimer's disease, senile dementia and multi-infarct dementia, and among the neurological diseases may be mentioned multiple sclerosis and head traumata. As an example of collagenosis may be mentioned rheumatoid arthritis. It has been found that amyloid appears both as a primary (S-AL) and a secondary (S-AA) phenomenon in addition to the main diagnosis in senile system amyloidosis (S-TTR) and other diseases. The amino acid sequence in the amyloid may varity depending on the primary disease.

However, it is to be noted that rheumatoid arthritis is not always connected with the occurrence of amyloid. On the other hand, amyloid is sometimes detected as a first symptom of other afflictions than rheumatoid arthritis, such as cranial trauma, myeloma or Alzheimer's disease.

It has now surprisingly been found that certain lignan derivatives have the property of suppressing the formation of amyloid when administered to a host afflicted with a state of amyloidosis without giving rise to the severe side effects associated with the prior art compositions for this purpose. These derivatives are acetals of podophyllotoxin-β-D-glucopyranoside and 4'-demethylpodophyllotoxin-β-D-glucopyranoside having the general formula

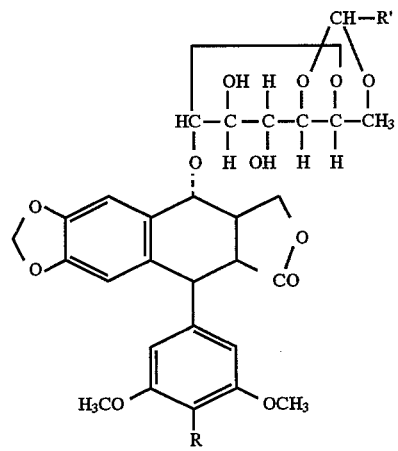

wherein R is OH or OCH$_3$, and R' is an alkyl, aryl or heterocyclic residue.

Such compounds are previously known from the literature, such as Arzneimittel-Forschung 11 (1961) 459, and British Patent No. 823,068.

Thus, the present invention refers to the use of acetals of podophyllotoxin-β-D-glucopyranoside and 4'-demethylpodophyllotoxin-β-D-glucopyranoside having the formula (I)

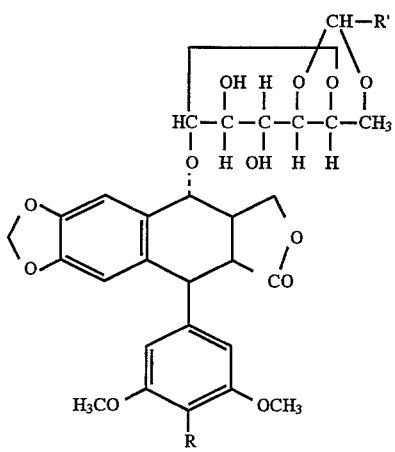

wherein R is OH or OCH₃, and R' is an alkyl, aryl or heterocyclic residue, for the preparation of a pharmaceutical composition for the treatment or prophylaxis of a state of amyloidosis.

The invention further refers to a method of treating a host afflicted with a state of amyloidosis, which comprises administering to said host an effective amount of at least one of the acetals of podophyllotoxin-β-D-glucopyranoside and 4'-demethylpodophyllotoxin-β-D-glucopyranoside having the formula

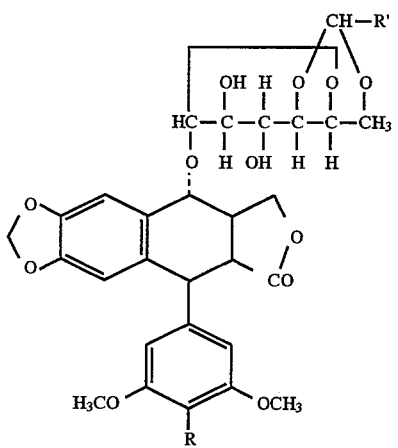

wherein R is OH or OCH₃, and R' is an alkyl, aryl or heterocyclic residue. The host in question is usually a mammal, and most preferably a human.

In the general formula (I), R' is preferably a methyl, phenyl or thenyl group.

The compounds encompassed by the above formula may be used singly as pure compounds, or together in a mixture with each other.

The acetals depicted in formula (I) may be obtained as described in Brit. Patent 823,068 by treatment of podophyllotoxin-β-D-glucopyranoside or 4'-demethylpodophyllotoxin-β-D-glucopyranoside with the appropriate aldehyde in the presence of a Lewis acid, e.g. anhydrous zinc chloride. The aldehyde may also be replaced by its dialkyl acetal as described in Journal of Medicinal Chemistry 14 (1971) 937 for the analogous compounds in the epipodophyllotoxin series.

A crude mixture of modified glycosides of lignans, among them podophyllotoxin-4,6-O-benzylidene-β-D-glucopyranoside and 4'-demethylpodophyllotoxin-4,6-O-benzylidene-β-D-glucopyranoside, is known under the name "Proresid", and has been used in therapy since the 1950's. In addition to these two glucosides, the mixture contains a number of other lignan derivatives, flavones and flavonols, and some of these constituents are known to be strongly mutagenic. The exact composition of "Proresid" can vary within wide limits.

Originally, "Proresid" was used as an antitumour agent, but it has later been found that its antitumour effect is limited in comparison with other cytostatics, and its use for this purpose has therefore been discontinued. It has later been found that "Proresid" can be used in the treatment of rheumatoid arthritis with good results, and in the treatment of rheumatoid arthritis with good results, and in the treatment of occasional cases of secondary amyloidosis with moderate results (M. Ahlmén et al; Clinical Rheumatology, 1987, No. 1, p. 27–28).

However, the use of Proresid in amyloidosis therapy has been associated with very strong side effects, primarily on the gastrointestinal tract. these side effects have made it impossible to administer the therapeutic agent in doses sufficiently high to exert a really useful therapeutic effect. The side effects, especially diarrhoea, have been so severe, in spite of an administration, of antidiarrhoea agents at the same time, that it has often been necessary to discontinue the treatment.

By the use of the pure compounds defined by the present formula (I), however, the incidence of undesirable side effects has been drastically reduced. Thus, in a study of 15 patients being treated with "Proresid", 11 of these patients had to be treated regularly with an antidiarrhoea agent to be able to cope with the severe gastrointestinal side effects. When the same group of patients were subsequently switched over to a mixture of pure podophyllotoxin-4,6-O-benzylidene -β-D-glucopyranoside and 4'-demethylpodophyllotoxin-4,6-O-benzylidene-β-D-glucopyranoside, only two patients needed a treatment with an antidiarrhoea agent. This clearly shows that the compounds defined by the present invention give a much lower incidence of undesirable gastrointestinal side effects. They can therefore be administered in greater amounts to give an acceptable therapeutic effect, without giving an increased incidence of undersirable side effects.

This very marked improvement in the incidence of undesirable side effects is completely unexpected and could not be predicted from the prior art. It is well-known to those skilled in the art that podophyllotoxin has a very strong irritant effect and that this effect is most pronounced in the gastrointestinal tract. These effects were believed to be common to all podophyllo-toxin derivatives, and it could not be predicted that the removal of certain minor constituents from the "Proresid" mixture would leave specific podophyllotoxin derivatives which would only exhibit small and acceptable side effects while still retaining their useful therapeutic effects.

As further advantages may be mentioned that the compounds of the present invention can be used to give a more predictable and secure effect, as they are pure and well-defined compounds. In contrast to this, the "Proresid" is a not very well-defined mixture having a composition which varies considerably, as is stated above. The compounds of the invention can be obtained in a high purity of above 99%. This of course makes it easier to use the present compounds in therapy to obtain predictable results.

It has also been shown that the above-mentioned combination of benzylidenated podpohyllotoxin glycosides has a toxicity value LD 50 of 3000 to 5000 mg/kg p.o., while the toxicity of "Proresid" has an LD 50 value of 550–850 mg/kg p.o. This is a further advantage of the present invention.

The compounds have previously been known to have a number of other pharmacodynamic effects. Thus, they suppress the activity of lymphatic B- and T-cells ("killer cells"), and they can therefore be used to counteract reactions of immunity. They also inhibit cell division, especially in the metaphase, due to the influence on microtubuline.

According to the invention, the desired compounds are formulated into suitable pharmaceutical compositions. Such compositions usually comprise carriers, excipients and other auxiliary substances which are commonly used in formulating such compositions. The pharmaceutical compositions may be formulated for enteral, oral, parenteral or topical administration, and they may be in a solid form, such as tablets, powder, hard or soft capsules, suppositories or vagitories, a more or less semi-liquid form, such as ointments, gels and creams, or in a liquid form, such as solutions, emulsions or suspensions. They may contain further conventional additives, and also other therapeutically active agents. It lies within the competence of a person skilled in the art to prepare a suitable composition when the way of administration and other conditions for the administration are known.

The dose may be established by one skilled in the art, taking into account such factors as the type and severity of the illness, the way of administration, the age and condition of the patient, etc. A suitable dose has been found to lie within the range from about 0.1 to about 20 mg per kg of body weight and day.

As has been stated previously, the defined compounds are used in pharmaceutical preparations for the treatment or prophylaxis of states of amyloidosis. Such states may be associated with diseases of the following groups:
1. Mental illness or illnesses, such as Alzheimer's disease, senile dementia and multi-infarct dementia
2. Neurological diseases, such as multiple sclerosis and head traumata
3. Collagenoses or connective tissue diseases, such as rheumatoid arthritis.

The compounds of the invention have been subjected to a number of pharmaceutical, toxicological and clinical investigations in order to determine their therapeutic properties. Some results of these investigations are described in the following disclosure.

Pharmacodynamics in Human Lymphocytes

The 4,6-O-benzylidene derivatives of podophyllotoxin-β-D-glucopyranoside and 4'-demethylpodophyllotoxin-β-glucopyranoside-β-D-glucopyranoside according to the invention were tested in vitro on four human lymphoblastic cell lines. The concentrations were selected to mimic clinical conditions. The derivatives blocked the cells mainly in the $G_2$ phase of the cell cycle.

A minor retardation was also observed in the S and M phases. In comparison with two other "metaphase" blockers, podophyllotoxin and taxol, the present derivatives exhibited a different and dose/time dependent pattern of cell cycle retardation.

In a study, patients were treated for a time varying between 29 and 132 weeks for the diagnosis secondary amyloidosis with Reumacon®, which is a 10:1 mixture by weight of podophyllotoxin-4,6-O-benzylidene-β-D-glucopyranonside and 4'-demethylpodophyllotoxin-4,6-O-benzylidene-β-D-glucopyranoside. The renal clearance, the protein leakage and the blood creatinine were determined before and after the treatment. The results are summarized in the following table:

| Pat No. | Treatment Period/ Weeks | Clearance mL/min | | U-Protein g/24 hrs | | B-creatinine | |
|---|---|---|---|---|---|---|---|
| | | I | II | I | II | I | II |
| 1 | 96 | 96 | 102 | 0.13 | 0.06 | 61 | 60 |
| 2 | 60 | 72 | 114 | 0.1 | 0.05 | 73 | 63 |
| 3 | 48 | 108 | 120 | 0.15 | <0.01 | 41 | 40 |
| 4 | 60 | 114 | 78 | 0.11 | 0.05 | 85 | 76 |
| 5 | 132 | 44 | 64.8 | 0.2 | 0.14 | 101 | 117 |
| 6 | 132 | 130 | 177 | 2.35 | 0.36 | 42 | 53 |
| 7 | 29 | 71 | 82 | 0.4 | 1.11 | 63 | 59 |

The values in the columns "I" are the baseline values, and the values in the columns "II" are the values obtained after the treatment.

In a successful treatment, the renal clearance should increase, the protein leakage should decrease, and a reduction of the blood creatinine should be achieved. It will be seen that for six of the seven patients, the renal clearance has increased, and the protein leakage has decreased remarkably. The creatinine value is somewhat uncertain, as it partly is dependent on the food intake.

In addition, it has been shown that Reumacon® inhibits mitogen-induced lymphocyte proliferation and immunoglobulin synthesis in a dose/time dependent manner, a property which may be useful to determine a suitable therapeutic dose level.

We claim:
1. A method of treating a host afflicted with a state of secondary amyloidosis, which comprises administering to said host an effective amount of at least one acetal of podophyllotoxin-β-D-glucopyranoside or of 4'-demethylpodophyllotoxin-β-D-glucopyranoside having the general formula

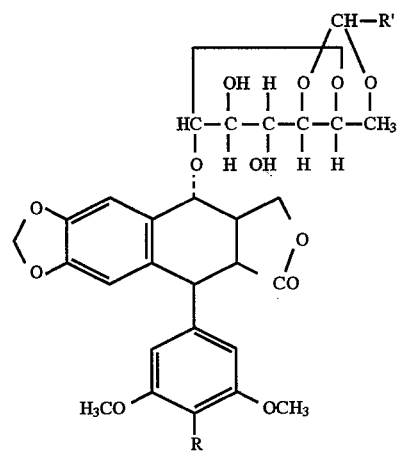

wherein R is OH or $OCH_3$, and R' is an alkyl, aryl or heterocyclic residue.

2. A method according to claim 1, wherein said state of amyloidosis is associated with mental illness.

3. A method according to claim 2, wherein said mental illness is Alzheimer's disease, senile dementia or multi-infarct dementia.

4. A method according to any one of claims 1–3, wherein said effective amount is from 0.1 to 20 mg per kg of body weight and day.

* * * * *